United States Patent
Qin et al.

(10) Patent No.: US 10,913,714 B2
(45) Date of Patent: Feb. 9, 2021

(54) PYRROLE SULFONYL DERIVATIVE, PREPARATION METHOD AND MEDICAL USE THEREOF

(71) Applicants: JIANGSU CAREPHAR PHARMACEUTICAL CO., LTD, Nanjing (CN); NANJING CAREPHAR SHENGHUI PHARMACEUTICAL CO., LTD, Nanjing (CN)

(72) Inventors: Yinlin Qin, Jiangsu Province (CN); Mei Su, Jiangsu Province (CN); Qiu Jin, Jiangsu Province (CN); Tao Chen, Jiangsu Province (CN); Jianhua Jiang, Jiangsu Province (CN)

(73) Assignees: JIANGSU CAREPHAR PHARMACEUTICAL CO., LTD, Jiangsu (CN); NANJING CAREPHAR SHENGHUI PHARMACEUTICAL CO., LTD, Jiangsu (CN)

( * ) Notice: Subject to any disclaimer, the term of this patent is extended or adjusted under 35 U.S.C. 154(b) by 0 days.

(21) Appl. No.: 15/547,522

(22) PCT Filed: Nov. 11, 2015

(86) PCT No.: PCT/CN2015/094255
§ 371 (c)(1),
(2) Date: Jul. 31, 2017

(87) PCT Pub. No.: WO2016/119505
PCT Pub. Date: Aug. 4, 2016

(65) Prior Publication Data
US 2018/0009749 A1 Jan. 11, 2018

(30) Foreign Application Priority Data
Jan. 27, 2015 (CN) .......................... 2015 1 0040549

(51) Int. Cl.
| | | |
|---|---|---|
| A61K 31/454 | (2006.01) | |
| A61K 31/402 | (2006.01) | |
| A61K 31/4025 | (2006.01) | |
| C07D 207/48 | (2006.01) | |
| C07D 405/04 | (2006.01) | |
| C07D 401/12 | (2006.01) | |
| C07D 413/12 | (2006.01) | |
| C07D 403/04 | (2006.01) | |
| A61K 31/404 | (2006.01) | |

(52) U.S. Cl.
CPC ......... *C07D 207/48* (2013.01); *C07D 401/12* (2013.01); *C07D 405/04* (2013.01); *C07D 413/12* (2013.01); *A61K 31/402* (2013.01); *A61K 31/404* (2013.01); *A61K 31/4025* (2013.01); *A61K 31/454* (2013.01); *C07D 403/04* (2013.01)

(58) Field of Classification Search
None
See application file for complete search history.

(56) References Cited

FOREIGN PATENT DOCUMENTS

WO    WO 2014075575    *    5/2014    ........... C07D 207/48

* cited by examiner

*Primary Examiner* — Samantha L Shterengarts
(74) *Attorney, Agent, or Firm* — PROI Intellectual Property US; Klaus Michael Schmid

(57) ABSTRACT

The present invention relates to a new pyrrole sulfonyl derivative, and a preparation method and medical use thereof. In particular, the present invention relates to a pyrrole sulfonyl derivative as represented by general formula (I), a preparation method thereof, a pharmaceutical composition comprising the derivative, and a use thereof as a therapeutic agent, in particular as a gastric acid secretion inhibitor and as potassium-competitive acid blockers (P-CABs), wherein each substituent group of general formula (I) is the same as that defined in the description.

17 Claims, No Drawings

PYRROLE SULFONYL DERIVATIVE, PREPARATION METHOD AND MEDICAL USE THEREOF

TECHNICAL FIELD

The Invention relates to a new pyrrole sulfonyl derivative and its preparation methods, a pharmaceutical composition comprising the derivative and its uses as therapeutic agents, in particular as a gastric acid secretion inhibitor and as potassium-competitive acid blockers (P-CABs).

BACKGROUND ART

The proton pump inhibitors, represented by omeprazole, have been widely used in clinical applications for treating such diseases as peptic ulcer, reflux esophagitis and Zollinger-Ellison syndrome (ZES) since 1988. It is found from long-term clinical applications that existing proton pump inhibitors have limitations in pharmacokinetics and pharmacodynamics, such as the effect of administration time on efficacy of medicine, the slow effect of nocturnal acid breakthrough, the instability under acidic condition (more likely to be enteric-coated preparation) and the dependence on enzyme CYP450 (resulting in significant individual differences), etc.

Potassium-Competitive Acid Blockers (P-CABs) may restrain $K^+$ in enzyme $H^+/K^+$-ATP competitively through a direct and reversible process. Compared with traditional proton pump inhibitors, P-CABs are characterized by lipotropy, alkalescence, high dissociation constant and stability under low pH condition. In acid environment, P-CABs may combine with enzyme $H^+/K^+$-ATP in an ionized form, preventing $H^+$ and acid secretion being delivered into gastral cavity and increasing the pH value in the stomach rapidly. It is found from animal experiments and clinical studies that, P-CABs take effects rapidly and can achieve maximum therapeutic effect in 1 h; the blood concentration and the oral administration dosage are linearly dependent, thus the optimum acid suppression effect can be easily reached.

Although a series of P-CABs has been disclosed by far, new compounds with more abundant structure types and better druggability still need to be developed. Through unremitting efforts, the Inventor designed a compound with a structure as shown in Formula (I) and discovered the outstanding effect and functions of the compound with such structure.

SUMMARY OF THE INVENTION

The Application provides a gastric acid secretion inhibitor with a structure as shown in Formula (I); the application method of which is described as follows:

The Application provides a compound with a structure as shown in Formula (I), or its tautomer, mesomer, raceme, enantiomer, diastereoisomer, or its mixture form or pharmaceutically acceptable salt:

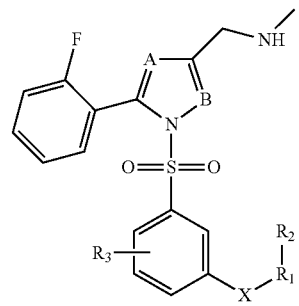

Wherein, A and B are independently selected from N or $CR_4$; R is selected from hydrogen, halogen and alkyl;

X is selected from O and $NR_5$; $R_5$ is selected from hydrogen and alkyl;

$R_1$ is selected from alkyl and heterocyclic alkyl; wherein, said alkyl and heterocyclic alkyl are further substituted by one or more substituents selected from hydrogen, halogen and alkyl;

$R_2$ is selected from alkyl sulfonyl, heterocyclic alkyl, alkoxy, alkyl acyl, phenoxy and alkyl amino; wherein, said alkyl sulfonyl, heterocyclic alkyl, alkoxy, alkyl acyl, phenoxy and alkyl amino are further substituted by one or more substituents selected from hydrogen, halogen and alkyl;

$R_3$ is selected from hydrogen, halogen and alkyl;

Further, A and B are selected from $CR_4$ and $R_4$ is selected from hydrogen.

Further, said compound is selected from:

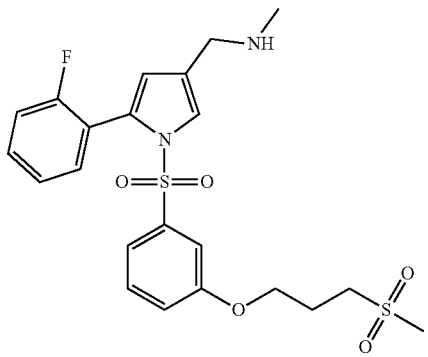

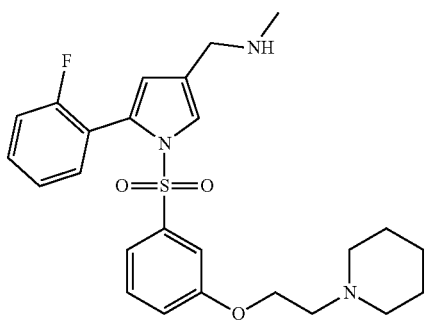

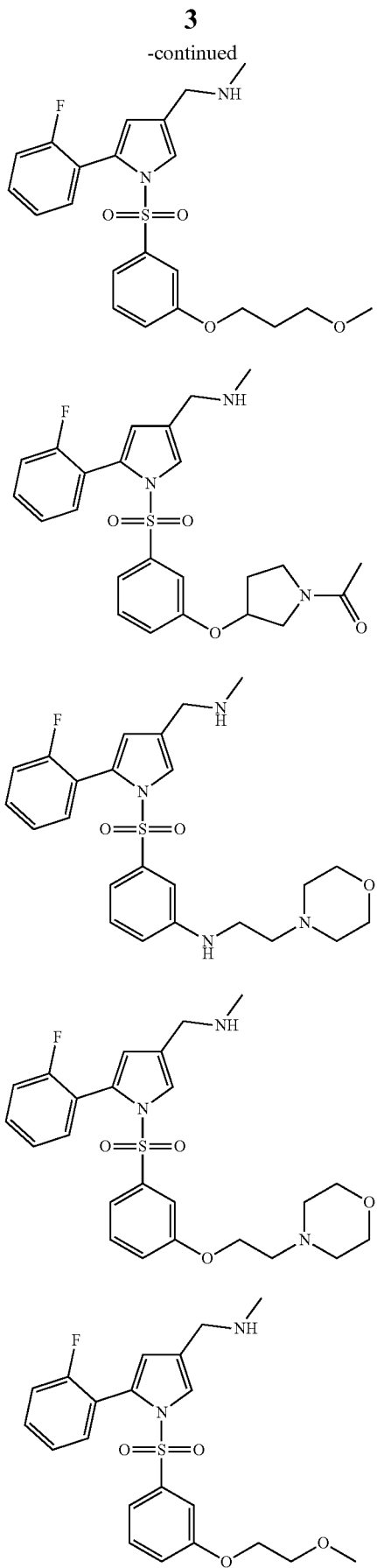
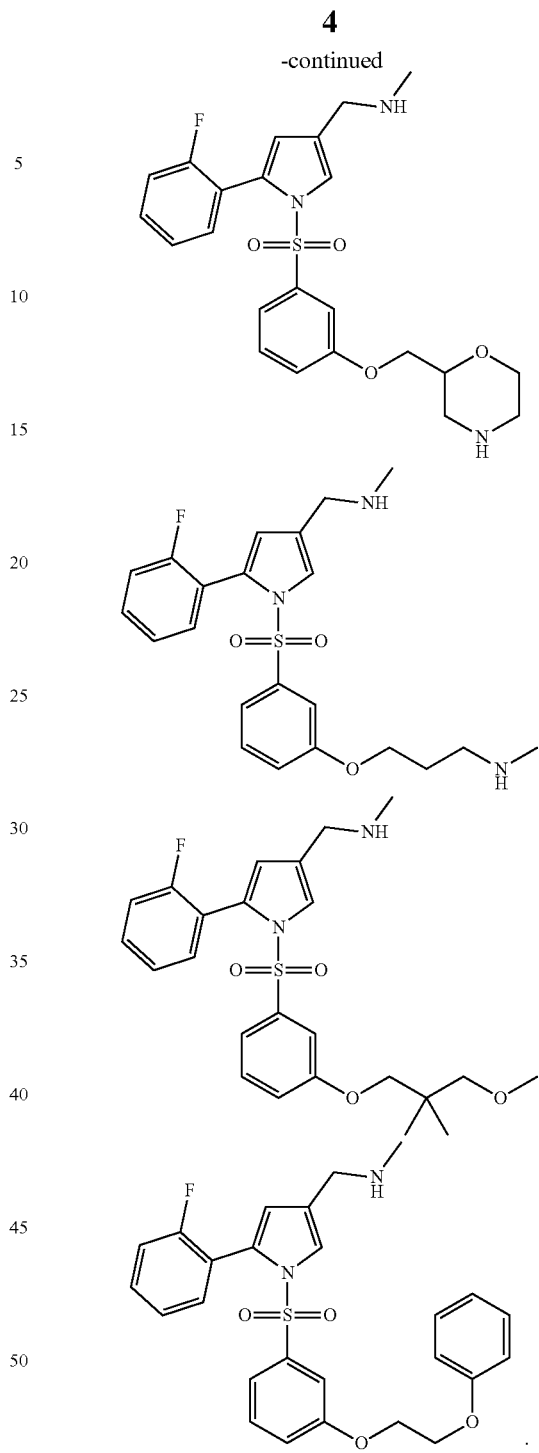

The Invention further relates to a pharmaceutical composition; said pharmaceutical composition contains an effective dose of the compound according to any of claims 1-3, or its tautomer, mesomer, raceme, enantiomer, diastereoisomer, or its mixture form or pharmaceutically acceptable salt and acceptable carriers, excipients, or thinner for medicine.

In another aspect, the Invention relates to a method for inhibiting gastric acid secretion; the method comprises an effective dose of the compound as shown in Formula (I) or its tautomer, mesomer, raceme, enantiomer, diastereoisomer, or its mixture form or pharmaceutically acceptable salt, or the pharmaceutical composition containing the compound is administered to the patient who needs treatment.

In another aspect, the Invention relates to the usage of the compound as shown in Formula (I) or its tautomer, mesomer, raceme, enantiomer, diastereoisomer, or its mixture form or pharmaceutically acceptable salt, or the pharmaceutical composition containing the compound in preparing inhibitor H+/K+-adenosine triphosphatase (H+/K+-ATPase).

In another aspect, the Invention relates to the usage of the compound as shown in Formula (I) or its tautomer, mesomer, raceme, enantiomer, diastereoisomer, or its mixture form or pharmaceutically acceptable salt, or the pharmaceutical composition containing the compound in preparing potassium-competitive acid blockers (P-CABs).

The Invention provides the usage of the medicine for treating or preventing peptic ulcer, Zollinger-Ellison syndrome, gastritis, erosive esophagitis, reflux esophagitis, symptomatic gastroesophageal reflux disease, Barrett esophagitis, functional dyspepsia, *Helicobacter pylori* infection, gastric cancer, gastric malt lymphoma, anabrosis caused by non-steroidal anti-inflammatory drugs (NSAIDs), or hyperacidity or anabrosis due to postoperative stress; or the method for preparing the medicine for inhibiting gastrointestinal bleeding caused by peptic ulcer, acute stress ulcer, hemorrhagic gastritis or invasive stress; wherein, peptic ulcer is selected from gastric ulcer, duodenal ulcer and marginal ulcer; said symptomatic gastroesophageal reflux disease is selected from nonerosive reflux disease, and gastroesophageal reflux disease without oesophagitis.

DETAILED DESCRIPTION

Unless otherwise stated, the following terms used in the Description and the Claims have the following implication.

"Alkyl" refers to saturated aliphatic hydrocarbon group, comprising the linear chain or branched chain group with 1-20 carbon atoms, preferably the medium sized alkyl with 1-6 carbon atoms, such as methyl, ethyl, propyl, 2-propyl, n-butyl, isobutyl, tert-butyl and amyl. and more preferably the lower alkyl with 1-4 carbon atoms, such as methyl, ethyl, propyl, 2-propyl, n-butyl, isobutyl and tert-butyl. Alkyl can be either substituted or un-substituted; when substituted, the preferred groups are halogen, $C_2$-$C_6$ alkenyl, $C_6$-$C_{10}$ aryl, $C_5$-$C_{10}$ ceteroary, halogenated $C_1$-$C_6$ alkyl, 4-8-element hetero-alcyl, hydroxyl, $C_1$-$C_6$ alkoxy, and $C_6$-$C_{10}$ aryloxy. "Hetero-naphthenic group" refers to monocyclic group or condensed ring group; there are 5-9 annular atoms in the ring, wherein, one or two annular atoms are heteroatoms selected from N, O and $S(O)_p$ (wherein, p is an integer from 0-2) and the rest annular atoms are C. These rings can have one or more double bonds, but no a electronic system that is fully conjugated. The non-restrictive example of the un-substituted hetero-alcyl comprises pyrrolidinyl, piperidine (1-position only), piperazine (1-position only), morpholine substituted group, thiomorpholine substituted group, homopiperazine (1-position only), etc. Hetero-alcyl can be either substituted or un-substituted; when substituted, the substituent is preferably one or more; more preferably one, two or three and further more preferably one or two; said substituent is selected from hydrogen, hydroxyl, sulfhydryl, oxo, lower alkyl, lower alkoxy, lower naphthenic base, lower hetero-alcyl, lower halogenated alkoxy, alkyl sulphanyl, halogen, lower halogenated alkyl, lower hydroxyalkyl, lower naphthenic base alkylidene, lower hetero-alcyl alkylidene, aryl, ceteroary, alkoxy carbonyl, amino, alkyl amino, alkyl sulfonyl, aryl sulfonyl, alkyl amino sulfonyl, aryl amino sulfonyl, alkyl sulfonyl amino, aryl sulfonyl amino, alkyl amino carbonyl, aryl amino carbonyl, alkyl carbonyl amino and aryl carbonyl amino. Unless otherwise indicated, the example of miscellaneous alicyclic base comprises but not limited to morpholinyl, piperazinyl, piperidyl, azacyclo-butyl, pyrrolidyl, hexahydro-aza-tropylium group, oxacyclo-butyl, tetrahydrofuranyl, tetrahydrothiophenyl, oxazolidinyl, thiazolidinyl, isoxazolidinyl, tetrahydropyranyl, sulfomorpholinyl, quinuclidinyl and imidazolinyl; each group is as previously mentioned; the example can be dicyclic, such as 3,8-biaza-dicyclic [3.2.1] octane, 2,5-bi-aza-dicyclic [2.2.2] octane or octahydro-pyrazine [2,1-c] [1,4] oxazine; wherein, the hetero-alcyl (and its derivatives) include the ion forms. "Alkoxy" represents —O— (un-substituted alkyl) and —O (substituted naphthenic base). The representative example comprises but not limited to methoxyl, ethyoxyl, propoxy, butoxy, cyclopropoxy, cyclobutoxy, cyclopentyloxy and cyclohexyloxy, etc. "Alkyl sulfonyl" represents —S($O_2$)-alkyl.

"Alkyl amino" represents —NH-alkyl.

"Alkyl acyl" represents

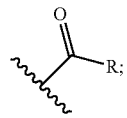

R is lower alkyl.

"Hydroxy" represents —OH group.

"Halogen" represents fluorine, chlorine, bromine or iodine; fluorine or chlorine is preferred.

The so-called "optionally" means the subsequently described events or circumstances may or may not occur; the description includes that the events or circumstances may or may not occur and the description includes two possibilities as occurrence and nonoccurrence of the events or circumstances.

In some embodiments, "substituted by one or more groups" refers to that one, two, three or four hydrogen atoms in specific atom or group are substituted by the same or different group selected from the groups in a specified scope.

The "pharmaceutically acceptable salt" refers to the salts that keep the bio-availabilities and properties of the parent compound. Such salts comprise:

(1) Acid addition salt, which is obtained through the reaction of the free alkali of the parent compound with an inorganic acid or an organic acid; the inorganic acid comprises hydrochloric acid, hydrobromic acid, nitric acid, phosphoric acid, metaphosphoric acid, sulfuric acid, sulphurous acid, perchloric acid, etc.; the organic acid comprises acetic acid, propionic acid, crylic acid, oxalic acid, (D) or (L) malic acid, fumaric acid, maleic acid, hydroxybenzoic acid, γ-hydroxybutyric acid, methoxybenzoic acid, phthalic acid, methanesulfonic acid, ethanesulfonic acid, naphthalene-1-sulfoacid, naphthalene-2-sulfoacid, p-toluenesulfonic acid, salicylic acid, tartaric acid, citric acid, lactic acid, mandelic acid, succinic acid, malonic acid, etc.

(2) The salt generated from the acidic proton in parent compound being substituted by a metal ion or from the complexing combination with an organic alkali; the metal ion is selected form alkali metal ion, alkaline earth metal ion and aluminium ion; the organic alkali is selected form cholamine, diethanolamine, triethanolamine, tromethamine and n-methylglucosamine, etc.

The "pharmaceutical composition" refers to the mixture of one or more of the compounds or its pharmaceutically acceptable salt, solvate, aquo-complex or prodrug and other chemical components as the pharmaceutically acceptable carriers. The pharmaceutical composition is to facilitate the process of drug delivery to animals.

The "pharmaceutical carrier" refers to the inactive ingredients in the pharmaceutical composition that neither cause obvious irritating effect to the organism, nor interferes the bioactivities and properties given to the compound, which comprise but not limited to calcium carbonate, calcium phosphate, various saccharides (such as lactose and mannitol), starch, cyclodextrin, magnesium stearate, cellulose, magnesium carbonate, acrylic polymers or methacrylate polymers, gel, water, polyethylene glycol, propylene glycol, ethylene glycol, castor oil or hydrogenated castor oil or polyethoxy hydrogenated castor oil, sesame oil, corn oil and peanut oil, etc.

In above pharmaceutical composition, in addition to the pharmaceutically acceptable carriers, it may also comprise adjuvants commonly used in pharmacy, such as antibacterial agent, antifungal agent, antimicrobial agent, quality preservation agent, color matching agent, solubilizing agent, thickening agent, surface active agent, complexing agent, protein, amino acid, fat, saccharides, vitamin, mineral substance, microelement, sweetening agent, pigment, essence or their combinations.

DETAILED DESCRIPTION OF THE PREFERRED EMBODIMENTS

The Invention is further described in combination with the following embodiments, which are not limitations to the scope of the Invention.

Embodiment 1

Preparation of 1-(5-(2-fluorobenzene)-1-((3-(3-methoxy propoxy)phenyl)sulfonyl)-1H-pyrrole-3-yl)-N-methyl methylamine (EXP 1)

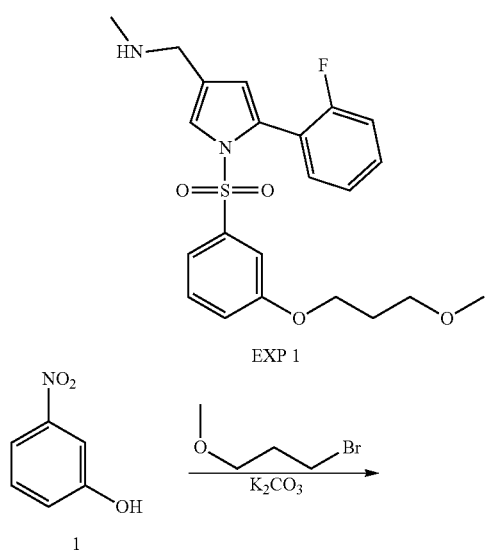

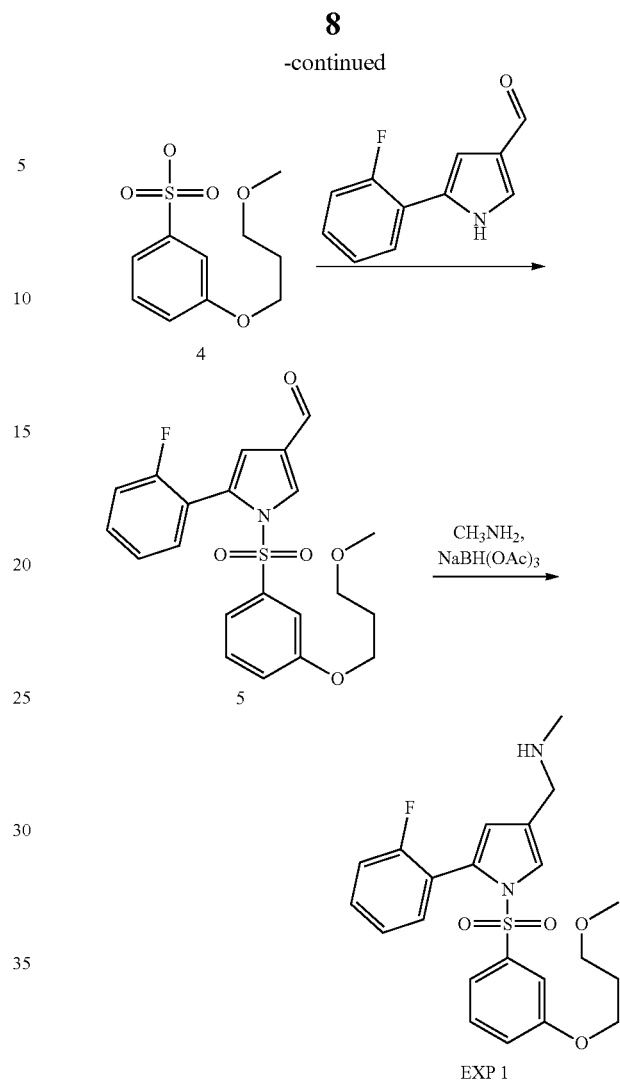

1) Preparation of 1-(3-methoxy propoxy)-nitrobenzene (Compound 2)

Dissolving 3-nitrophenol (Compound 1, 1.0 g, 7.19 mmol), potassium carbonate (2.9 g, 21.6 mmol) and 1-bromo-3-methoxy propane (1.65 g, 10.79) in anhydrous DMF (20 mL) and stirring it at 90° C. for staying overnight; adding water (50 mL) and extracting it with ethyl acetate (50 mL×3); combining organic phases for drying and concentration, thus, the yellow solid 1-(3-methoxy propoxy)-nitrobenzene (Compound 2, 1.5 g, 100% yield) is obtained.

2) Preparation of 1-(3-methoxy propoxy)-phenylamine (Compound 3)

Dissolving 1-(3-methoxy propoxy)-nitrobenzene (Compound 2, 1 g, 4.74 mmol), RaneyNi (100 mg) in anhydrous methanol (20 mL) and stirring it under hydrogen atmosphere at ambient temperature for staying overnight; filtering it to get filter liquor for spin drying, thus the solid 1-(3-methoxy propoxy)-phenylamine (Compound 3, 0.80 g, 91% yield) is obtained.

3) Preparation of 1-(3-methoxy propoxy)-benzene sulfonyl chloride (Compound 4)

Adding sodium nitrite (571 mg, 8.29 mmol) in batches into the acetic acid (10 mL) and hydrochloric acid water solution (2N, 10 mL) of 1-(3-methoxy propoxy)-phenylamine (Compound 3, 1.0 g, 5.52 mmol) at 0° C.; stirring it for 25 min at 0° C. after feeding to obtain Solution I; adding cuprous chloride (190 mg, 1.1 mmol) into the acetic acid solution (10 mL, 2N) of sulfur dioxide at 0° C. to obtain Solution II; adding Solution I into Solution II by drops at 0° C.; rising the temperature up to ambient temperature naturally thereafter and stirring the solution for reaction for 3 h; extracting it with ethyl acetate (150 mL×3); combining organic phases for drying, concentration and column chromatography (petroleum ether:ethyl acetate=20:1), thus the yellow oily substance 1-(3-methoxy propoxy)-benzene sulfonyl chloride (Compound 4, 800 mg, 55% yield) is obtained.

4) Preparation of 5-(2-fluorobenzene)-1-((3-(3-methoxy propoxy)phenyl)sulfonyl)-1H-pyrrole-3-formaldehyde (Compound 5)

Adding t-BuOK (233 mg, 2.08 mmol) in the anhydrous THF (5 mL) of 5-(2-fluorobenzene)-1H-pyrrole-3-formaldehyde (200 mg, 1.04 mmol) and stirring it for reaction for 30 min at 0° C.; adding 15-crown-5 (542 mg, 2.08 mmol) and 1-(3-methoxy propoxy)-benzene sulfonyl chloride (Compound 4, 412 mg, 2.08 mmol) respectively after the reaction; rising the temperature up to ambient temperature naturally after feeding and stirring the solution for reaction for 90 min; adding ice water (50 g) for quenching after the reaction and extracting it with ethyl acetate (50 mL×3); combining organic phases for drying, concentration and column chromatography (petroleum ether:ethyl acetate=8:1), thus the yellow oily substance 5-(2-fluorobenzene)-1-((3-(3-methoxy propoxy)phenyl)sulfonyl)-1H-pyrrole-3-formaldehyde (260 mg, 60% yield) is obtained.

5) Preparation of 1-(5-(2-fluorobenzene)-1-((3-(3-methoxy propoxy)phenyl)sulfonyl)-1H-pyrrole-3-yl)-N-methyl methylamine (EXP 1)

Dissolving 5-(2-fluorobenzene)-1-((3-(3-methoxy propoxy)phenyl)sulfonyl)-1H-pyrrole-3-formaldehyde (Compound 5, 500 mg, 1.19 mmol), acetic acid (144 mg, 2.39 mmol) and methylamine alcohol solution (1 mL) in anhydrous methanol (3 mL) and stirring it for 4 h at ambient temperature; adding $NaBH_3CN$ (212 mg, 3.59 mmol) and stirring for 60 min; adding ice water (30 g) for quenching and extracting it with ethyl acetate (50 mL×3); combining organic phases for drying, concentration and column chromatography, thus the yellow solid 1-(5-(2-fluorobenzene)-1-((3-(3-methoxy propoxy)phenyl)sulfonyl)-1H-pyrrole-3-yl)-N-methyl methylamine (EXP 1, 100 mg, 20%) is obtained.

HPLC: 99.4%; MS (ESI) m/z: [M+H]$^+$=433.0; $^1$H-NMR (400 MHz, DMSO-d6) δ: 8.72 (s, 1H), 7.78 (d, 1H), 7.46-7.55 (m, 2H), 7.21-7.32 (m, 3H), 6.85-7.11 (m, 2H), 6.83-6.85 (m, 1H), 6.44 (d, 1H), 3.95-4.02 (m, 4H), 3.47 (t, 2H), 3.32 (s, 3H), 2.52 (m, 3H), 1.94 (t, 2H) ppm.

Embodiment 2: Preparation of 1-(3-(3-((2-(2-fluorobenzene)-4-((methylamino)methyl)-1H-yl)sulfonyl)phenoxy)pyrrolidine-1-yl)ethyl-1-ketone (EXP 2)

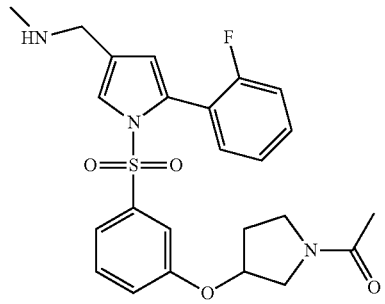

EXP 2

Obtaining the white solid compound 1-(3-(3-((2-(2-fluorobenzene)-4-((methylamino)methyl)-1H-yl)sulfonyl)phenoxy)pyrrolidine-1-yl)ethyl-1-ketone (EXP 2, 65% yield) by reference to the preparation method in Embodiment 1.

HPLC: 94.8%; MS (ESI) m/z: [M+H]$^+$=472; $^1$H-NMR (400 MHz, DMSO-d6) δ: 8.75 (s, 1H), 7.78 (s, 1H), 7.48-7.53 (m, 2H), 7.35 (t, 1H), 7.22-7.25 (m, 2H), 7.04-7.09 (m, 2H), 6.86-6.88 (m, 1H), 6.45 (d, 1H), 4.77-4.79 (m, 1H), 4.01 (s, 2H), 3.39-3.64 (m, 4H), 2.55 (d, 3H), 1.86-2.09 (m, 4H) ppm.

Embodiment 3: Preparation of 1-(5-(2-fluorobenzene)-1-((3-(2-methoxy ethyoxyl)phenyl)sulfonyl)-1H-pyrrole-3-yl)-N-methyl methylamine (EXP 3)

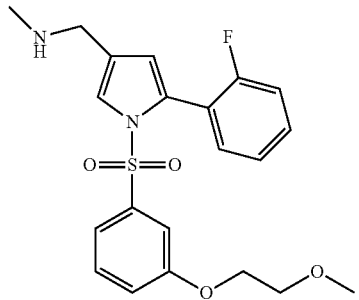

EXP3

Obtaining the compound 1-(5-(2-fluorobenzene)-1-((3-(2-methoxy ethyoxyl)phenyl)sulfonyl)-1H-pyrrole-3-yl)-N-methyl methylamine (EXP 3, 80 mg, 10% yield) by reference to the preparation method in Embodiment 1.

HPLC: 96.5%; MS (ESI) m/z: [M+H]$^+$=419.2; $^1$H-NMR (400 MHz, MeOD) δ: 7.44 (d, 1H), 7.42 (m, 1H), 7.37 (t, 1H), 7.04-7.19 (m, 5H), 6.89 (t, 1H), 6.28 (d, 1H), 4.03 (t, 2H), 3.72 (t, 2H), 3.63 (s, 2H), 3.42 (d, 3H), 2.38 (s, 3H) ppm.

Embodiment 4: Preparation of 1-(5-(2-fluorobenzene)-1-((3-(3-methyl sulphonyl propoxy)phenyl)sulfonyl)-1H-pyrrole-3-yl)-N-methyl methylamine (EXP 4)

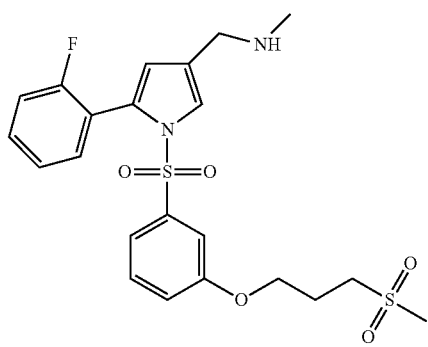

Obtaining the compound 1-(5-(2-fluorobenzene)-1-((3-(3-methyl sulphonyl propoxy)phenyl)sulfonyl)-1H-pyrrole-3-yl)-N-methyl methylamine (EXP 4, 70 mg, 20% yield) by reference to the preparation method in Embodiment 1.

HPLC: 94.28%; MS (ESI) m/z: $[M+H]^+=481.2$; $^1$H-NMR (400 MHz, MeOD) δ: 7.45 (m, 2H), 7.34 (t, 1H), 7.06-7.19 (m, 5H), 6.89 (t, 1H), 6.28 (d, 1H), 4.06 (t, 2H), 3.59 (s, 2H), 3.34 (m, 2H), 3.42 (d, 3H), 3.01 (s, 3H), 2.36 (s, 3H), 2.27 (m, 2H) ppm.

Embodiment 5: Preparation of 1-(5-(2-Fluorobenzene)-1-((3-(2-Morpholinyl Ethyoxyl)Phenyl)Sulfonyl)-1H-Pyrrole-3-Yl)-N-Methyl Methylamine (EXP 5)

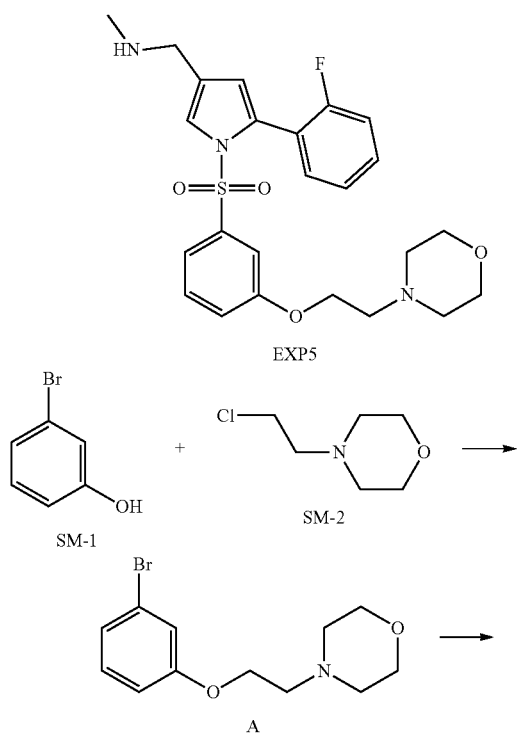

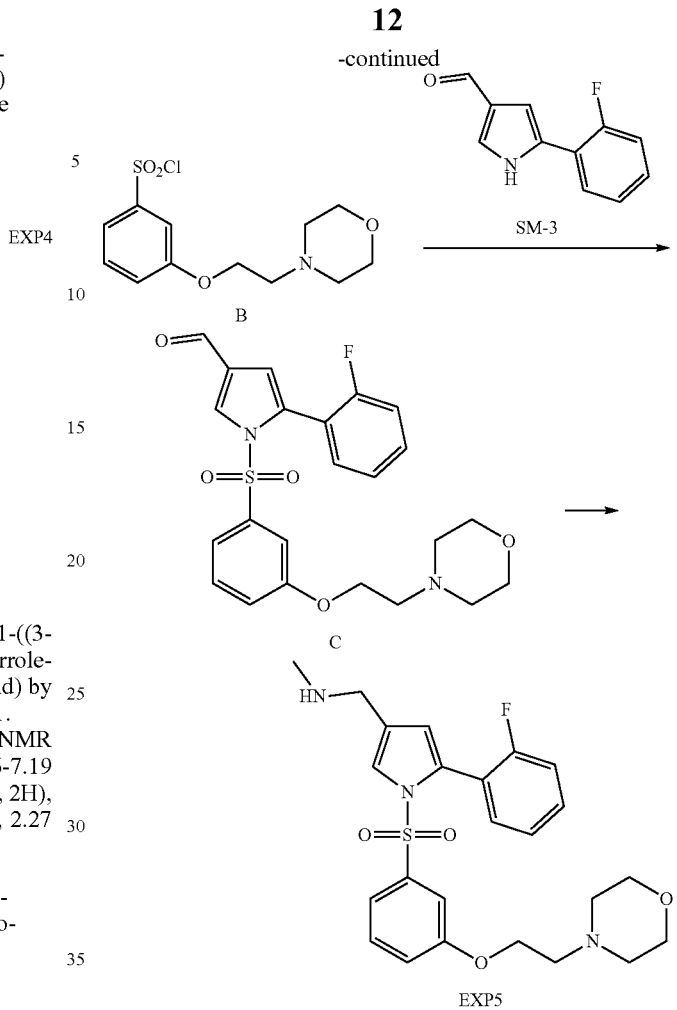

1) Preparation of 4-(2-(3-bromine phenoxy)ethyl)morpholine (Compound A)

Dissolving 3-bromophenol (SM-1, 5 g, 29 mmol, 1 eq), N-(2-chloroethyl) morpholine (SM-2, 4.3 g, 29 mmol, 1 eq) and potassium carbonate (8 g, 58 mmol, 2 eq) in anhydrous DMF (50 ml) and stirring it at ambient temperature for staying overnight; conducting TLC test for complete reaction; adding water and extracting it with EA; evaporating the organic layer for column chromatography isolation, thus the Compound A (9 g, 90% yield) is obtained.

2) Preparation of 3-(2-Morpholinyl Ethyoxyl) Benzene Sulfonyl Chloride (Compound B)

Dissolving Compound A (4 g, 14 mmol, 1 eq) in anhydrous THF (50 ml) and cooling it to −78° C.; adding n-BuLi (13 ml, 21 mmol, 1.5 eq) and stirring for 1 h at −78° C.; inletting sulfur dioxide gas into the reaction mixture for 20 min and heating up from −78° C. to 0° C. in 2 h; Concentrating and evaporating the reaction mixture to dryness and adding DCM (50 ml) and N-chlorosuccinimide (NCS 2.8 g, 21 mmol, 1.5 eq) and stirring for 12 h; conducting column chromatography isolation to the reaction mixture directly, thus the Compound B (2 g, 50% yield) is obtained.

3) Preparation of 5-(2-Fluorobenzene)-1-((3-(2-Morpholinyl Ethyoxyl)Phenyl)Sulfonyl)-1H-Pyrrole-3-Formaldehyde (Compound C)

Dissolving compound SM-3 (1.2 g, 6.5 mmol, 1 eq) in THF (15 ml) and cooling it to 0° C.; adding NaH (0.4 g, 9.8 mmol, 1.5 eq) and stirring for 0.5 h at 0° C.; Adding Compound B (2 g, 6.5 mmol, 1 eq) and 15-crown-5 (2 g) into the reaction mixture add stirring for 0.5 h at ambient temperature; adding water; extracting with EA; evaporating the organic layer for column chromatography isolation, thus the Compound C (700 mg, 30% yield) is obtained.

4) Preparation of 1-(5-(2-Fluorobenzene)-1-((3-(2-Morpholinyl Ethyoxyl)Phenyl)Sulfonyl)-1H-Pyrrole-3-Yl)-N-Methyl Methylamine (EXP 5)

Dissolving Compound C (0.7 g, 1.53 mmol, 1 eq) in methyl alcohol (5 ml); adding methylamine alcohol solution (4 ml) and adding acetic acid (2 ml) at 0° C. for stirring for 2 h; adding sodium cyanoborohydride (0.9 g, 15.3 mmol, 10 eq) and stirring for 14 h; conducting LC-MS test for complete reaction; adding sodium bicarbonate solution and extracting it with EA; evaporating the organic layer, thus the compound (EXP 5) (100 mg, 15% yield) is obtained.

HPLC: 96.06%; MS (ESI) m/z: $[M+H]^+$=474.6; $^1$H-NMR (400 MHz, DMSO-d6) δ: 7.42-7.51 (m, 3H), 7.17-7.27 (m, 3H), 7.08-7.12 (m, 1H), 7.02 (d, 1H), 6.87 (s, 1H), 6.32 (s, 1H), 4.03 (t, 2H), 3.57 (t, 4H), 3.50 (s, 2H), 2.66 (t, 2H), 2.45-2.50 (m, 4H), 2.24 (s, 3H) ppm.

Embodiment 6: Preparation of 3-((2-(2-Fluorobenzene)-4-((Methylamino)Methylene)-1H-Pyrrole-1-Yl)Sulfonyl)-N-(2-Morpholinyl Ethyl) Henylamine (EXP 6)

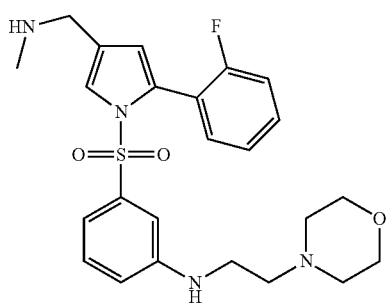

EXP6

Obtaining the compound 3-((2-(2-fluorobenzene)-4-((methylamino)methylene)-1H-pyrrole-1-yl)sulfonyl)-N-(2-morpholinyl ethyl) henylamine (EXP 6, 100 mg, 20% yield) by reference to the preparation method in Embodiment 5.

HPLC: 96.99%; MS (ESI) m/z: $[M+H]^+$=473.6; $^1$H-NMR (400 MHz, DMSO-d6) δ: 7.57 (d, 1H), 7.48 (q, 1H), 7.17-7.24 (m, 3H), 7.08-7.12 (m, 1H), 6.85 (d, 1H), 6.55-6.58 (m, 1H), 6.38 (s, 1H), 6.11 (t, 1H), 3.83 (s, 2H), 3.59 (s, 4H), 3.03 (q, 2H), 2.39-2.44 (m, 9H) ppm.

Embodiment 7: Preparation of 3-(3-((2-(2-fluorobenzene)-4-((methylamino)methylene)-1H-pyrrole-1-yl)sulfonyl)phenoxy)-N-methyl-n-propylamine (EXP 7)

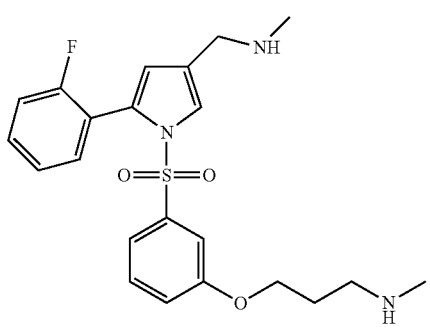

EXP7

Obtaining the compound 3-(3-((2-(2-fluorobenzene)-4-((methylamino)methylene)-1H-pyrrole-1-yl)sulfonyl)phenoxy)-N-methyl-n-propylamine (EXP 7, 80 mg, 40% yield) by reference to the preparation method in Embodiment 5.

HPLC: 95.84%; MS (ESI) m/z: $[M+H]^+$=432.2; $^1$H-NMR (400 MHz, DMSO-d6) δ: 7.40-7.51 (m, 3H), 7.18-7.25 (m, 3H), 7.03-7.13 (m, 1H), 6.83 (s, 1H), 6.31 (s, 1H), 3.39 (t, 2H), 3.46 (s, 2H), 2.59 (t, 2H), 2.29 (s, 3H), 1.81 (m, 2H) ppm.

Embodiment 8: Preparation of 1-(5-(2-fluorobenzene)-1-((3-(morpholinyl-2-yl-methoxyl)phenyl)sulfonyl)-1H-pyrrole-3-yl)-N-methyl methylamine (EXP 8)

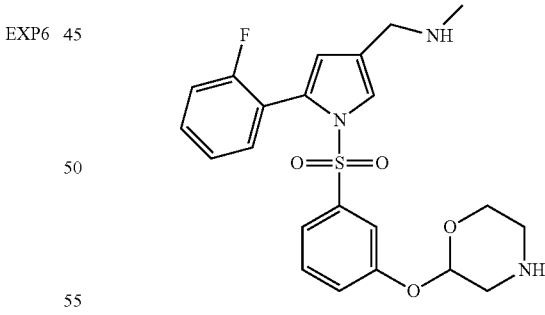

EXP8

Obtaining the compound 1-(5-(2-fluorobenzene)-1-((3-(morpholinyl-2-yl-methoxyl)phenyl)sulfonyl)-1H-pyrrole-3-yl)-N-methyl methylamine (EXP 8, 100 mg, 20% yield) by reference to the preparation method in Embodiment 5.

HPLC: 95.75%; MS (ESI) m/z: $[M+H]^+$=460.2, $[M+Na]^+$=482.2; $^1$H-NMR (400 MHz, DMSO-d6) δ: 7.44-7.47 (m, 3H), 7.18-7.28 (m, 3H), 7.04-7.13 (m, 1H), 7.02 (d, 1H), 6.86 (s, 1H), 6.31 (d, 1H), 3.86 (d, 2H), 3.65-3.75 (m, 2H), 3.44-3.48 (m, 3H), 2.82-2.85 (m, 1H), 2.64-2.67 (m, 3H), 2.45-2.51 (m, 1H), 2.23 (s, 3H) ppm.

Embodiment 9: Preparation of 1-(5-(2-fluorobenzene)-1-((3-(3-methoxy-2,2-dimethyl propoxy)phenyl)sulfonyl)-1H-pyrrole-3-yl)-N-methyl methylamine (EXP 9)

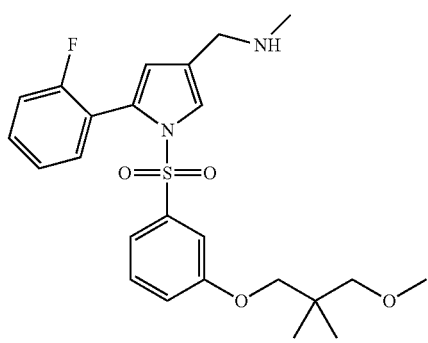

EXP9

Obtaining the compound 1-(5-(2-fluorobenzene)-1-((3-(3-methoxy-2,2-dimethyl propoxy)phenyl)sulfonyl)-1H-pyrrole-3-yl)-N-methyl methylamine (EXP 9, 59 mg, 15% yield) by reference to the preparation method in Embodiment 1.

HPLC: 96.4%; MS (ESI) m/z: [M+H]$^+$=461.5; $^1$H-NMR (400 MHz, DMSO-d6) δ: 7.85 (t, 1H), 7.68-7.75 (m, 3H), 7.46-7.49 (m, 2H), 7.27-7.35 (m, 2H), 6.80-6.83 (m, 1H), 6.34 (s, 1H), 3.79-3.85 (m, 4H), 3.61 (t, 2H), 3.26 (s, 3H), 2.38 (m, 3H), 0.89 (s, 6H) ppm.

Embodiment 10: Preparation of 1-(5-(2-Fluorobenzene)-1-((3-(2-Phenoxy Ethyoxyl)Phenyl)Sulfonyl)-1H-Pyrrole-3-Yl)-N-Methyl Methylamine (EXP 10)

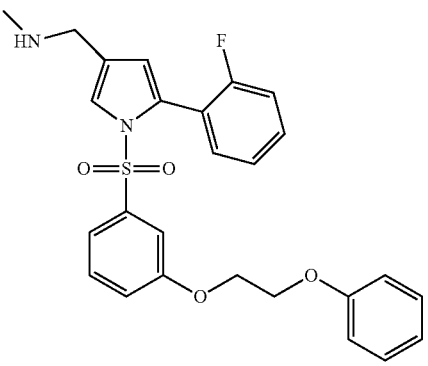

EXP10

Obtaining the compound 1-(5-(2-fluorobenzene)-1-((3-(2-phenoxy ethyoxyl)phenyl)sulfonyl)-1H-pyrrole-3-yl)-N-methyl methylamine (EXP 10, 74 mg, 25% yield) by reference to the preparation method in Embodiment 1.

HPLC: 98.4%; MS (ESI) m/z: [M+H]$^+$=481.5; $^1$H-NMR (400 MHz, DMSO-d6) δ: 7.65-7.81 (m, 4H), 7.46-7.50 (m, 2H), 7.25-7.33 (m, 4H), 6.89-6.93 (m, 4H), 6.13 (s, 1H), 4.51 (s, 4H), 3.61 (s, 2H), 3.21 (s, 3H) ppm.

Embodiment 11: Preparation of 1-(5-(2-Fluorobenzene)-1-((3-(2-Piperidine-1-Yl)Ethyoxyl)Phenyl)Sulfonyl)-1H-Pyrrole-3-Yl)-N-Methyl Methylamine (EXP 11)

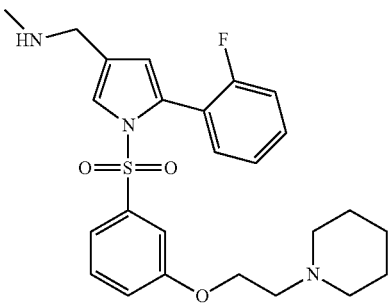

EXP11

Obtaining the compound 1-(5-(2-fluorobenzene)-1-((3-(2-piperidine-1-yl)ethyoxyl)phenyl)sulfonyl)-1H-pyrrole-3-yl)-N-methyl methylamine (EXP 11, 174 mg, 35% yield) by reference to the preparation method in Embodiment 1.

HPLC: 98.1%; MS (ESI) m/z: [M+H]$^+$=472.6; $^1$H-NMR (400 MHz, DMSO-d6) δ: 7.48-7.72 (m, 3H), 7.18-7.32 (m, 3H), 7.10-7.15 (m, 2H), 6.87 (s, 1H), 6.23 (s, 1H), 4.03 (t, 2H), 3.50 (s, 2H), 2.66 (t, 2H), 2.41-2.52 (m, 4H), 2.28 (s, 3H), 1.37-1.51 (m, 6H) ppm.

Embodiment 12: Preparation of 1-(5-(2-fluorobenzene)-1-((3-(2-methoxy phenyl)sulfonyl)-1H-pyrrole-3-yl)-N-methyl methylamine (EXP 12)

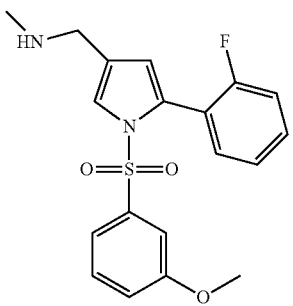

EXP12

Obtaining the compound 1-(5-(2-fluorobenzene)-1-((3-(2-methoxy phenyl)sulfonyl)-1H-pyrrole-3-yl)-N-methyl methylamine (EXP 12, 105 mg, 20% yield) by reference to the preparation method disclosed in the literature WO 2006036024, Journal of Medicinal Chemistry (2012), 55(9), 4446-4456.

HPLC: 95.4%; MS (ESI) m/z: [M+H]$^+$=375.5.

Embodiment 11: Preparation of 5-(2-fluorophenyl)-N-methyl-1-(3-pyridyl sulfonyl)-1H-pyrrole-3-methamine fumarate (TAK-438)

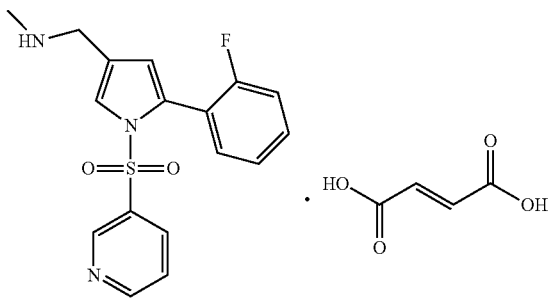

TAK-438

Obtaining the compound 5-(2-fluorophenyl)-N-methyl-1-(3-pyridyl sulfonyl)-1H-pyrrole-3-methamine fumarate (TAK-438, 5.0 g, 40% yield) by reference to the preparation method disclosed in the literature WO 2006036024, Journal of Medicinal Chemistry (2012), 55(9), 4446-4456.

HPLC: 99.8%; MS (ESI) m/z: [M+H]$^+$=347.1; $^1$H-NMR (500 MHz, DMSO-d6) δ: 10.71 (s, 3H), 8.86 (dd, 1H), 8.55 (d, 1H), 7.83-7.85 (m, 1H), 7.78 (s, 1H), 7.55-7.60 (m, 1H), 7.46-7.50 (m, 1H), 7.13-7.19 (m, 1H), 7.07-7.10 (m, 1H), 6.49-6.51 (m, 3H), 3.94 (s, 2H), 2.50 (s, 3H) ppm.

Embodiment 14: Preparation 2-(3-((2-(2-fluorophenyl)-4-((methylamine)methyl)-1H-pyrrole-1-yl)sulfonyl)phenoxy)-N-methylacetamide (EXP 14)

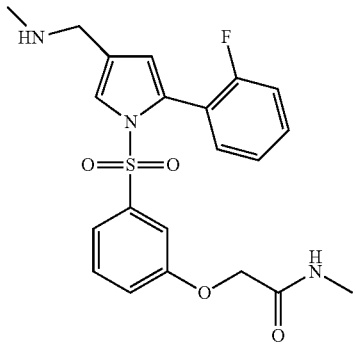

EXP14

Obtaining the compound 2-(3-((2-(2-fluorophenyl)-4-((methylamine)methyl)-1H-pyrrole-1-yl)sulfonyl)phenoxy)-N-methylacetamide (EXP 14, 50 mg, 40% yield) by reference to the preparation method disclosed in the literature WO 2014075575.

HPLC: 96.4%; MS (ESI) m/z: [M+H]$^+$=432.3; $^1$H-NMR (400 MHz, DMSO-d6) δ: 7.75 (s, 1H), 7.39-7.49 (m, 2H), 7.27-7.29 (m, 1H), 7.05-7.17 (m, 4H), 6.96 (s, 1H), 6.39 (d, 1H), 4.45 (s, 2H), 4.09 (s, 2H), 3.31 (s, 3H), 2.79 (s, 3H), 2.68 (s, 3H) ppm.

Test Case 1:
Biological Evaluation on H$^+$/K$^+$-ATPase

The following screening assays in vitro are used to evaluate the inhibiting effect of the compound of the Invention on the enzymatic activity of H$^+$/K$^+$-ATPase. Experimental materials and instruments are as follows:

1) Rabbit gastric mucosal microsomes (enriched H$^+$/K$^+$-ATPase; extracted by the Applicant)
2) 5-triphosadenine ATP (Sigma-Aldrich: Art. No.: A2383)
3) Malachite green (Bailingwei Chemical Technology Co., Ltd.; Art. No.: 913120)
4) Ammonium molybdate (Bailingwei Chemical Technology Co., Ltd.; Art. No.: 128321)
5) Valinomycin (Bailingwei Chemical Technology Co., Ltd.; Art. No.: 227304)

Experimental Steps:
Reagent Preparation:
1) Dissolving the compound with DMSO to a proper concentration;
2) Buffer solution: 50 mmol/L HEPEs-Tris, pH=6.5, 5 mmol/L magnesium chloride, 10 μmol/L valinomycin;
3) Buffer solution: 50 mmol/L HEPEs-Tris, pH=6.5, 5 mmol/L magnesium chloride, 10 μmol/L valinomycin, 5 mmol/L potassium chloride;
4) ATP: diluting ATP to 5 mM with buffer solution 1;
5) Malachite green solution: dissolving 0.12% of malachite green in 2.5 mol/L of sulfuric acid; mixing 7.5% (V/V) of ammonium molybdate and 11% of Tween 20(V/V) in a proportion of 100:25:2;
6) The method for extracting rabbit gastric mucosal microsomes (enriched H$^+$/K$^+$-ATPase) is sucrose gradient centrifugation, i.e., washing the rabbit stomach with tap water and 3M NaCl solution respectively and removing the surface moisture with filter paper; adding the pre-cooled buffer solution (4 ml/g tissue) for homogenation in a tissue homogenizer for 2-5 min; removing the large tissue particles in a way of centrifugation (600 g, 10 mm) if any after homogenation; transferring the supernatant to a clean centrifugal tube for centrifugation for 30 min at 2000 g; then transferring the supernatant to a clean centrifugal tube for further centrifugation for 90 min at 100000 g; collecting the sediment; suspending the sediment in the homogenate and blowing it to be uniform; measuring the protein concentration with Bradford method; adjusting the concentration to 10 mg/ml; adding 7.5% Ficoll demixing fluid in an equal proportion for centrifugation for 60 min at 100000 g; collecting the middle layer (H$^+$/K$^+$-ATPase enriched gastric membranes) into a clean centrifugal tube; diluting it with 4-5 times of homogenate for further centrifugation for 90 min at 100000 g; collecting the sediment; suspending the sediment in the homogenate for homogenation with a glass homogenizer; measuring the protein concentration with Bradford method and adjusting the concentration to 22.5 mg/ml; freezing it under −80° C. for standby.

Experimental Process:
Adding 5 μL of gastric mucosal microsomes (H$^+$/K$^+$-ATPase) in 454 of buffer solution 2; adding 5 μL of the compound solution; adding 5 μL 5 mM of ATP to start the reaction for pre-reaction at 37° C. for 30 min; adding 15 μL of malachite green solution to terminate the reaction; balancing at ambient temperature for 20 min; reading the value of absorbed light at 620 nm.

Meanwhile, conducting another reaction with the same volume without potassium chloride for background, which will be subtracted when calculating the enzymatic activity.

The value of Compound IC$_{50}$ is calculated through the inhibition ratios at different concentrations.

Result: the value of Compound IC$_{50}$

The median inhibitory concentration (IC$_{50}$) of the compound provided by the Invention as shown in Formula I to the activity of H$^+$/K$^+$-ATPase

TABLE 1

The median inhibitory concentration (IC$_{50}$) of the compound to the activity of H$^+$/K$^+$-ATPase

| TAK-438 | EXP 1 | EXP 2 | EXP 3 | EXP 4 | EXP 5 | EXP 6 | EXP 7 | EXP 8 |
|---|---|---|---|---|---|---|---|---|
| +++ | +++ | ++ | ++ | +++ | ++ | ++ | ++ | ++ |

| EXP 9 | EXP 10 | EXP 11 | EXP 12 | EXP 14 |
|---|---|---|---|---|
| ++ | +++ | + | +++ | ++ |

+++ means IC$_{50}$ <100 nM;
++ means a scope of 0.1-1 μM;
+ means a scope of 1-5 μM Test Case 2:
Studies on the Effect of Compounds EXP 1, TAK-438 and EXP 12 on hERG Potassium Channel
Testing System
1) Cell culture: the hERG cell is cultured in a routine way, which is subcultured in a DMEM containing 10% of fetal calf serum and 250 μg/ml of G418.
2) Fluid preparation: the composition of the extracellular fluid used in the experiment of whole cell patch clamp comprises (mM): NaCl 145, MgCl21, KCl 4, Glucose 10, HEPES 10 and CaCl22; adjusting the pH value of NaOH to 7.4 and adjusting the value of osmotic pressure to 300 mOsm with sucrose. The composition of the intracellular fluid comprises (mM):KCl 140; MgCl 21; EGTA 5; HEPES 10 and Na2ATP 4; adjusting the pH value of KOH to 7.2 and adjusting the value of osmotic pressure to 290 mOsm with sucrose.

Main composition of the extracellular and intracellular fluid

| Reagent | Extracellular fluid (mM) | Intracellular fluid (mM) |
|---|---|---|
| CaCl2 | 2 | — |
| MgCl2 | 1 | 1 |
| KCl | 4 | 140 |
| NaCl | 145 | — |
| Glucose | 10 | — |
| HEPES | 10 | 10 |
| EGTA | — | 5 |
| Na2ATP | — | 4 |
| PH | 7.4 (adjusted with NaOH), osmolarity 300 mOsm | 7.2 (adjusted with KOH), osmolarity 290 mOsm |

Test Procedure
1) Electrophysiological recording: taking out one culture dish for each test; cleaning it with the extracellular fluid twice and placing it on the inverted microscope stage. The experiment of whole cell patch clamp is conducted at ambient temperature; the resistance at the microelectrode tip of the used borosilicate glass is 3-5 MQ.
2) Voltage stimulus plan and current record: clamping down the membrane potential to −80 mV under the whole-cell recording mode; giving +50 mV of depolarized voltage stimulus to the cell every 30 s and lasting for 2 s, then repolarizing it to −50 mV and lasting for 3 s, thus, the tail current of hERG can be extracted. Giving 50 ms, −50 mV repolarized voltage to the cell before depolarized voltage stimulus; the current recorded at such voltage is as the base line for calculating the tail current of hERG. Only the cells meet the recording standard can be used in the test of the compounds to be tested. The hERG tail current should be recorded stably at last for 3 min in the extracellular fluid before the compound is added. After perfusion of drugs, it can be regarded that the drug effect reaches a steady state if the change of the amplitude of hERG tail current is less than 5%. If the current fails to reach a steady state in 6 min, the test should also be terminated.
3) Testing standard: the membrane resistance in the experiment should be more than 1,000 MQ. The initial current should be more than 300 pA. The series resistance should be less than 12 MQ after the whole-cell recording mode is constructed. The leakage current is less than 10% of the ionic channel current (taking −80 pA as the peak value).
Data Analysis Using Clampex 10.2 to record the original data and saving the data in the format of *abf. Using pCLAMP 10.1 to conduct data collection and analysis. Selecting 4-5 sweeps when the current is in a steady state before the compound is added; calculating the average peak value to serve as the contrasted current amplitude. Selecting 4-5 sweeps when the current is in a steady state after the compound is added; calculating the average peak value to serve as the residual amplitude of the inhibited current. The inhibition ratio of the compound to be tested to hERG current is calculated as per the equation as:

% inhibition ratio={1−(current residual amplitude)/(contrasted current amplitude)}*100

After the inhibition ratio (average value±standard deviation) of the compound to be tested to the hERG current of different concentrations is obtained through the above computing method, the data with logistic equation should be fitted to obtain the value of IC$_{50}$.
Experiment Results

TABLE 2

Inhibition results of EXP 1, TAK-438 and EXP 12 to hERG current

| Compound name | Max. test concentration | Inhibition ratio of max. test concentration | IC$_{50}$ value |
|---|---|---|---|
| EXP 1 | 100 μM | 86.21 ± 1.67% | 18.69M |
| TAK-438 | 100 μM | 88.23 ± 3.18% | 15.93M |
| EXP 12 | 30 μM | 90.33 ± 2.16% | 3.95M |

Test Case 3:
Studies on the Effect of EXP 1, TAK-438 and EXP 14 on Gastric Acid Secretion Induced by Histamine
Experimental Materials
1) Animals SD rat, class SPF, male, 180-220 g; provided by Zhejiang Experimental Animal Center; production permit no.: SCXK (Z) 2014-0001.

2) Drugs and Reagents

Compound EXP 1, dissolved with a small amount of acetic acid (about 1.10N EXP 1), 0.9% sodium chloride solution to a clear liquid with needed concentration before use.

Compound TAK-438, dissolved with 0.9% sodium chloride solution to a clear liquid with needed concentration before use.

Compound EXP 14, dissolved with a small amount of acetic acid (about 1.10N EXP 14), 0.9% sodium chloride solution to a clear liquid with needed concentration before use.

0.9% of sodium chloride solution, provided by Anhui Double-Crane Pharmaceutical Co., Ltd.; batch no.: 131202. Histamine dihydrochloride: Aladdin; batch no.: H110868.

Chloral hydrate: provided by Sinopharm Chemical Reagent Co., Ltd.; batch no.: 20130314; prepared into 3% chloral hydrate solution with 0.9% sodium chloride solution.

Phenolphthalein: provided by Sinopharm Chemical Reagent Co., Ltd.; batch no.: F20110125; prepared into 3% phenolphthalein solution with 95% ethyl alcohol.

3) Instrument

Electronic scale: produced by Beijing Sartorius Scientific Instruments Co., Ltd.

Centrifuge: produced by Medical Equipment Factory of Shanghai Medical Instruments Co., Ltd.

Alkali burette: provided by Analysis & Research Office of China Medicine University Method and Result Fetching 60 SD rats of class SPF with a weight of 180-220 g; dividing the rats into 5 groups as per weights randomly, including Group EXP 1 (2 mg/kg), Group TAK-438 (2 mg/kg, as per free alkali), Group EXP 14 (2 mg/kg), Group negative control (normal saline of equal volume) and Group model control (normal saline of equal volume); 12 rats per group. Absolute diet for 24 h, water is allowed. After 24 h, administrating drugs to the tested compound groups A, B and C by gavage with a volume of 1 ml/100 g; each group is administered once; the negative control and model negative control groups are administrated by gavage with normal saline of equal volume. Narcotizing the rat with 300 mg/kg of chloral hydrate (1 ml/100 g) and fixing it onto the rat board; cutting to open the abdominal wall along the medio-ventral line from the mucronate cartilage with an incision of 2-3 cm; slightly pushing the left costal margin upward to expose the stomach in the incision. Ligaturing the pylorus thereunder (leave alone the adjacent blood vessels) and then suturing the abdominal incision. Giving histamine dihydrochloride (30 mg/10 m/kg) hypodermically to the rat 1 h after the tested compound or normal saline are administrated. Choking the rat to death with excessive $CO_2$ 3 h after the histamine is given; taking out the stomach and collecting the gastric contents for centrifugation at 3000 rpm/min; adjusting the PH value of the acid fluid to 7.0 with 0.1 mol/L of NaOH titration and then calculating the total acid content of the 3 h. Refer to Table 3 for results.

TABLE 3

The effect of the tested compound on gastric acid secretion induced by histamine

| Groups | Dosage (mg/kg) | Total acid content ($10^{-4}$ mol) | Acid inhibiting rate % |
|---|---|---|---|
| Negative control | / | 0.33 ± 0.12 | / |
| Model control | / | 1.09 ± 0.18 | / |

TABLE 3-continued

The effect of the tested compound on gastric acid secretion induced by histamine

| Groups | Dosage (mg/kg) | Total acid content ($10^{-4}$ mol) | Acid inhibiting rate % |
|---|---|---|---|
| EXP 1 | 2 | 0.49 ± 0.12** | 55.4 |
| TAK-438 | 2 | 0.52 ± 0.10** | 52.3 |
| EXP 14 | 2 | 0.65 ± 0.20** | 40.4 |

Note:
*$p < 0.05$,
**$p < 0.01$; compared with model groups

Test Case 4:

Acute Toxicity Test Reports for Gavage in Rats with Compound EXP 1 and TAK-438

Drugs: Compound EXP 1 (about 1.10N EXP 1), TAK-438 (the administration dosage is given as per free alkali)

Test content: single administration dosage: 2000 mg/kg, 600 mg/kg; administration by gavage: once; volume: 10 ml/kg; observing for 14 days for the rat's behavior and weight each day.

Animal: SD rat, class SPF, 180-220 g; provided by Zhejiang Experimental Animal Center; animal certificate no.: SCXK (Z) 2014-0001.

Experimental grouping: black group, Group of 600 mg/kg, Group of 2000 mg/kg; 4 rats each group; half male and half female. Experiment results:

EXP 1, single oral dose of 600 mg/Kg or 2000 mg/Kg; no death. As for the single oral dose of 600 mg/Kg, the impact on the rat's weight is not obvious.

TAK-438: 2000 mg/kg: all died; 600 mg/kg: inhibition of weight gain.

For the purposes of elaboration and understanding, the above invention is described in details in combination with examples and embodiments. It is obvious for a person skilled in the art that modifications and improvements can be made within the scope of the enclosed claims. Therefore, it should be understand that the above description is for illustration rather than limitation. Thus, the scope of the Invention should be determined by reference to the full scope of the enclosed claims and the equivalent authorized by the claims but not to the above Specification.

We claim:

1. A compound with a structure as shown in Formula (I), or its tautomer, mesomer, racemate, enantiomer, diastereoisomer, or its mixture form or pharmaceutically acceptable salt:

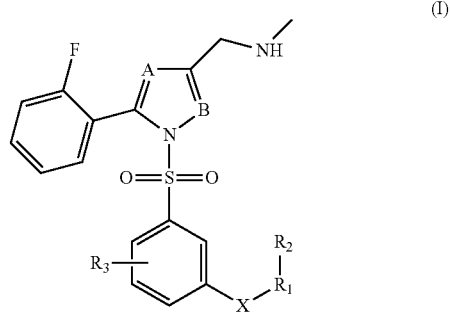

(I)

wherein, A and B are independently selected from N or CR$_4$; R$_4$ is selected from hydrogen, halogen and alkyl;

X is selected from O and NR$_5$; R$_5$ is selected from hydrogen and alkyl;

R$_1$ is selected from alkyl and heterocyclic alkyl; wherein, said alkyl and heterocyclic alkyl are further substituted by one or more substituents selected from hydrogen, halogen and alkyl;

R$_2$ is selected from alkyl sulfonyl, heterocyclic alkyl, alkoxy, alkyl acyl, phenoxy and alkyl amino; wherein, said alkyl sulfonyl, heterocyclic alkyl, alkoxy, alkyl acyl, phenoxy and alkyl amino are further substituted by one or more substituents selected from hydrogen, halogen and alkyl;

R$_3$ is selected from hydrogen, halogen and alkyl.

2. The compound according to claim 1, wherein A and B are CR$_4$; R$_4$ is hydrogen.

3. The compound according to claim 1, being selected from any of the following compounds:

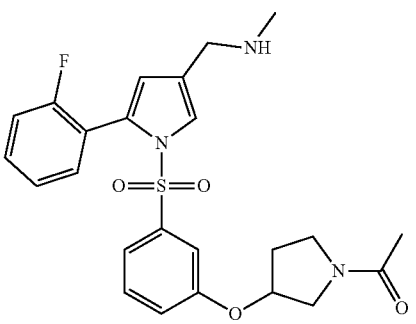

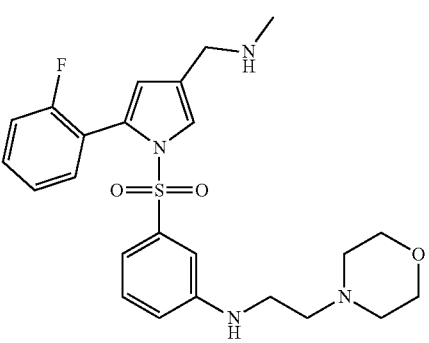

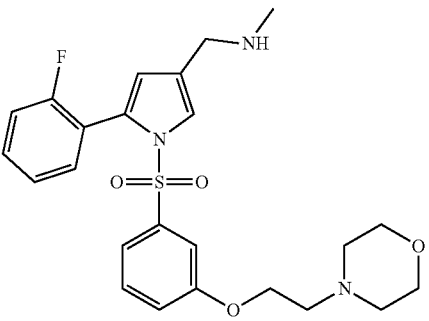

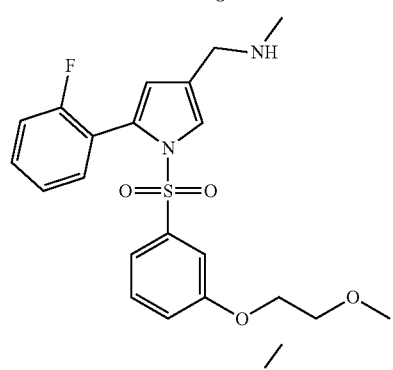

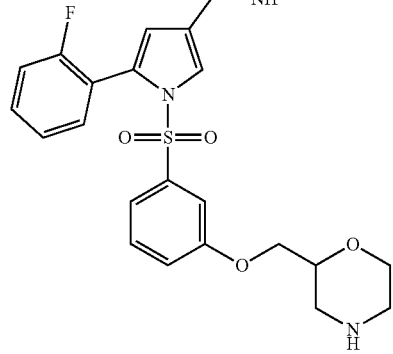

-continued

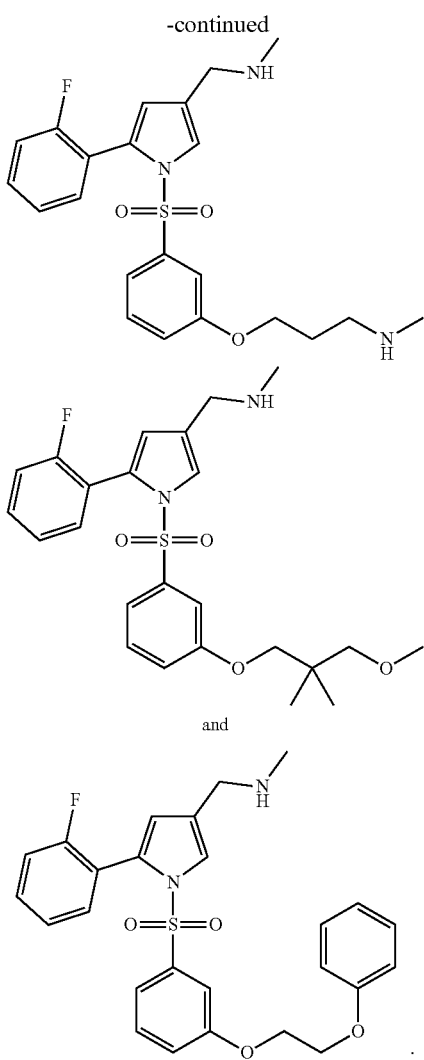

and

4. A pharmaceutical composition, comprising an effective dose of the compound according to claim 1, or its tautomer, mesomer, racemate, enantiomer, diastereoisomer, or its mixture form or pharmaceutically acceptable salt and acceptable carriers, excipients, or thinner for medicine.

5. The compound according to claim 1, wherein the compound is a gastric acid secretion inhibitor.

6. A method of manufacturing a pharmaceutical composition capable of inhibiting an H+/K+-ATPase inhibitor, comprising a step of incorporating into the pharmaceutical composition an effective amount of the compound according to claim 1.

7. The method according to claim 6, where the compound is a Potassium-Competitive Acid Blockers (P-CABs).

8. A method for treating a disease caused by taking non-steroidal anti-inflammatory drugs (NSAIDs), or due to postoperative stress; comprising a step of administering to a patient in need of such treatment an effective amount of a compound of claim 1.

9. The method according to claim 8, wherein the disease is selected from the group consisting of peptic ulcer, Zollinger-Ellison syndrome, gastritis, erosive esophagitis, reflux esophagitis, symptomatic gastroesophageal reflux disease, Barrett esophagitis, functional dyspepsia, *Helicobacter pylori* infection, gastric cancer, gastric malt lymphoma, anabrosis, hyperacidity and anabrosis.

10. A pharmaceutical composition according to claim 4, wherein A and B are $CR_4$: $R_4$ is hydrogen.

11. A pharmaceutical composition according to claim 4, wherein the compound is selected from any of the following compounds:

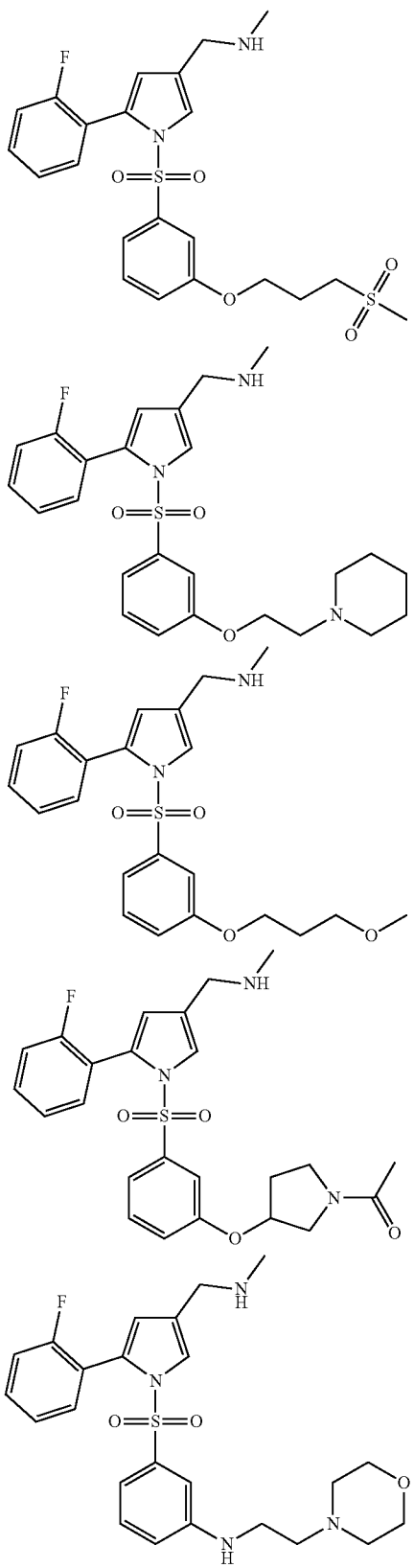

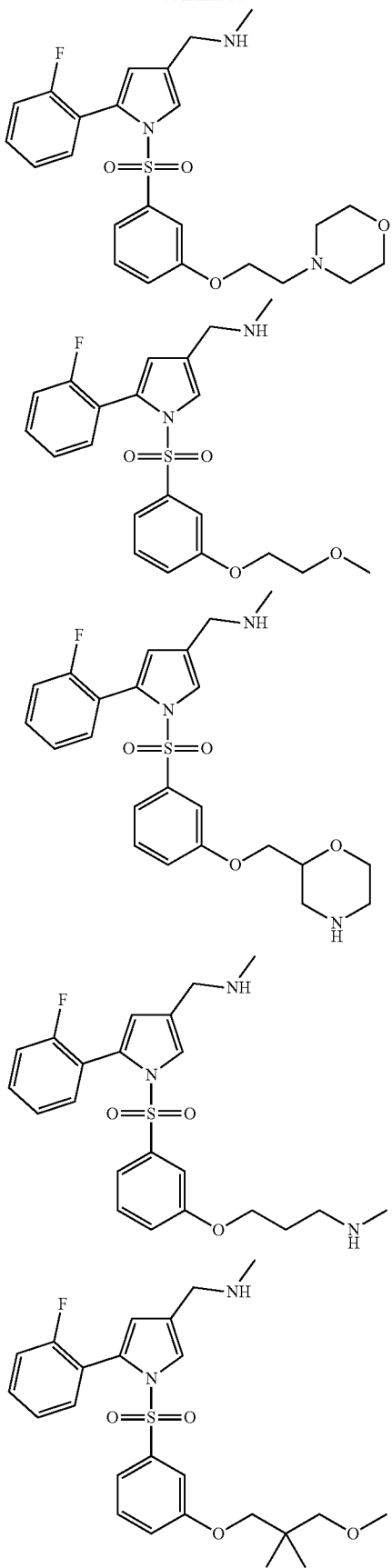

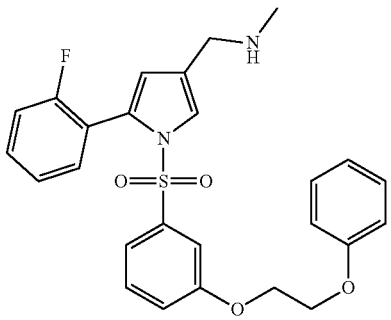

12. The compound according to claim 2, wherein the compound is a gastric acid secretion inhibitor.

13. The compound according to claim 3, wherein the compound is a gastric acid secretion inhibitor.

14. The pharmaceutical composition according to claim 4, wherein the pharmaceutical composition is a gastric acid secretion inhibitor.

15. The pharmaceutical composition according to claim 10, wherein the pharmaceutical composition is a gastric acid secretion inhibitor.

16. The pharmaceutical composition according to claim 11, wherein the pharmaceutical composition is a gastric acid secretion inhibitor.

17. The pharmaceutical composition according to claim 4, wherein the compound is selected from the group consisting of the following compounds:

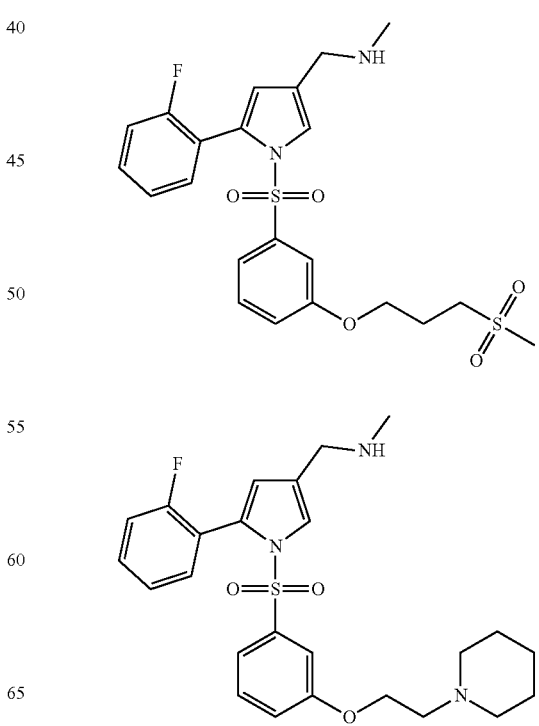

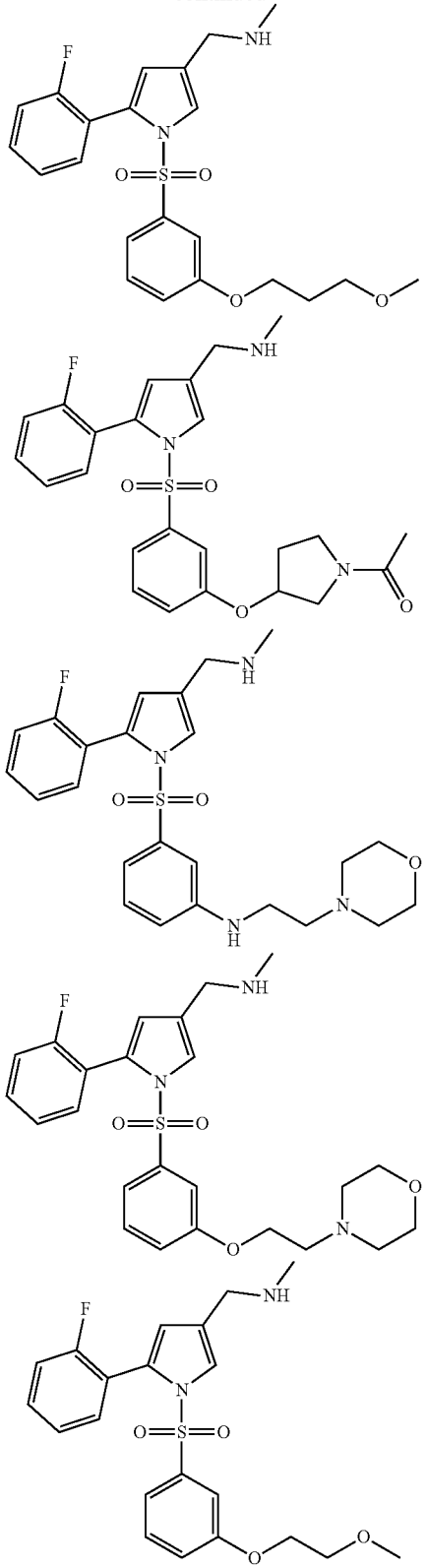
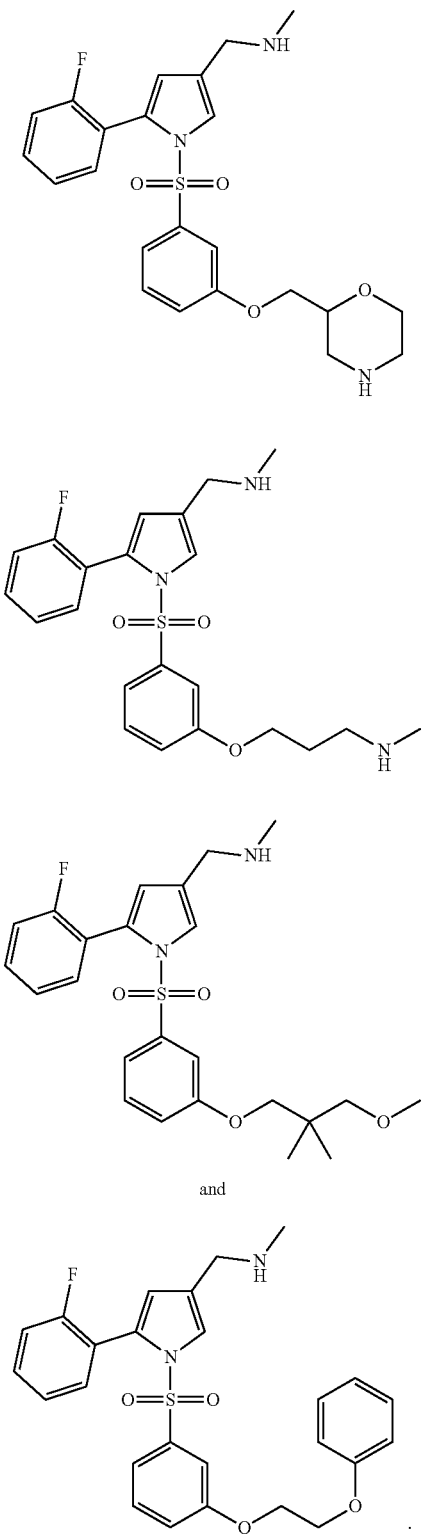
* * * * *